United States Patent
Choi et al.

(10) Patent No.: US 8,293,961 B2
(45) Date of Patent: Oct. 23, 2012

(54) CATALYTIC CRACKING PROCESS USING FAST FLUIDIZATION FOR THE PRODUCTION OF LIGHT OLEFINS FROM HYDROCARBON FEEDSTOCK

(75) Inventors: Sun Choi, Daejeon (KR); Yong Seung Kim, Daejeon (KR); Deuk Soo Park, Gyeonggi-do (KR); Suk Joon Kim, Daejeon (KR); Ji Min Kim, Daejeon (KR); Hong Chan Kim, Seoul (KR); Seung Hoon Oh, Daejeon (KR); Tae-Jin Kim, Daejeon (KR); Dae Hyun Choo, Busan (KR)

(73) Assignee: SK Innovation Co., Ltd., Seorin-Dong, Jongro-Gu, Seoul (KR)

( * ) Notice: Subject to any disclaimer, the term of this patent is extended or adjusted under 35 U.S.C. 154(b) by 196 days.

(21) Appl. No.: 11/996,319

(22) PCT Filed: Jun. 7, 2006

(86) PCT No.: PCT/KR2006/002172
§ 371 (c)(1),
(2), (4) Date: Jan. 21, 2008

(87) PCT Pub. No.: WO2007/108573
PCT Pub. Date: Sep. 27, 2007

(65) Prior Publication Data
US 2009/0012339 A1    Jan. 8, 2009

(30) Foreign Application Priority Data

Mar. 17, 2006  (KR) .................. 10-2006-0025005

(51) Int. Cl.
*C07C 4/06* (2006.01)

(52) U.S. Cl. .......... 585/651; 585/650; 585/648; 208/67; 208/113

(58) Field of Classification Search .................. 585/407, 585/418, 648, 650, 651, 653; 208/67, 70, 208/74, 85
See application file for complete search history.

(56) References Cited

U.S. PATENT DOCUMENTS

| | | |
|---|---|---|
| 4,065,379 A | 12/1977 | Soonawala et al. |
| 4,548,138 A | 10/1985 | Korenberg |
| 4,693,808 A | 9/1987 | Dewitz |
| 5,012,026 A | 4/1991 | Avidan et al. |
| 5,043,522 A | 8/1991 | Leyshon et al. |
| 5,372,704 A | 12/1994 | Harandi et al. |
| 5,770,043 A | 6/1998 | Ellis et al. |
| 6,267,873 B1 | 7/2001 | Das et al. |
| 6,307,117 B1 | 10/2001 | Tsunoda et al. |

(Continued)

FOREIGN PATENT DOCUMENTS

EP    0834540    4/1998

(Continued)

*Primary Examiner* — Tam M Nguyen
(74) *Attorney, Agent, or Firm* — McDermott Will & Emery

(57) ABSTRACT

Disclosed is a catalytic cracking process for the production of light olefins from a hydrocarbon feedstock using fast fluidization, which is a preferred process for more efficiently increasing the production of light olefin hydrocarbons. According to this invention, a fast fluidization regime is applied to a fluidized bed catalytic cracking process of producing light olefins using zeolite, such that a volume fraction and distribution of the catalyst sufficient to induce the catalytic cracking reaction can be provided, thus effectively enhancing the production of light olefin hydrocarbons, in particular, ethylene and propylene, at high selectivity.

19 Claims, 6 Drawing Sheets

U.S. PATENT DOCUMENTS

| | | |
|---|---|---|
| 6,342,153 B1 | 1/2002 | Guan et al. |
| 6,395,949 B1 | 5/2002 | Drake et al. |
| 6,548,725 B2 * | 4/2003 | Froment et al. ............... 585/653 |
| 6,602,920 B2 | 8/2003 | Hall et al. |
| 6,791,002 B1 | 9/2004 | Abrevaya et al. |
| 6,867,341 B1 | 3/2005 | Abrevaya et al. |
| 2001/0056217 A1 * | 12/2001 | Froment et al. ............... 585/653 |
| 2002/0061813 A1 * | 5/2002 | Wang et al. .................... 502/73 |
| 2002/0169350 A1 * | 11/2002 | Steffens et al. ............... 585/648 |
| 2003/0196932 A1 * | 10/2003 | Lomas ............................ 208/67 |
| 2005/0234281 A1 | 10/2005 | Bjorklund et al. |

FOREIGN PATENT DOCUMENTS

| | | |
|---|---|---|
| EP | 0908506 A1 | 4/1999 |
| JP | 2002513777 A | 5/2002 |
| RU | 2125079 C1 | 1/1999 |

* cited by examiner

CATALYTIC CRACKING PROCESS USING FAST FLUIDIZATION FOR THE PRODUCTION OF LIGHT OLEFINS FROM HYDROCARBON FEEDSTOCK

CROSS REFERENCE TO RELATED APPLICATIONS

This application is the 371 U.S. national phase of International Application No. PCT/KR2006/002172, filed Jun. 6, 2006, which claims priority to Korean Application No. 10-2006-0025005, filed on Mar. 17, 2006, both of which are incorporated by reference herein. The PCT application published in English as WO2007/108573 A1.

TECHNICAL FIELD

The present invention relates to a catalytic cracking process for the production of light olefins from a hydrocarbon feedstock using fast fluidization, and more specifically, to a catalytic cracking process for the production of light olefins from a hydrocarbon feedstock, in which the flow regime of a riser is maintained as a fast fluidization regime instead of a conventional dilute pneumatic conveying regime, thus more efficiently producing light olefin hydrocarbons.

BACKGROUND ART

These days, light olefins, in particular, light olefins such as ethylene or propylene, have been widely used in petrochemical industries. Generally, such light olefins have been mainly produced through steam cracking for thermally cracking (e.g., steam cracking) naphtha or kerosene in the presence of steam. Further, light olefin compounds have been limitedly produced as a by-product of FCC (Fluid Catalytic Cracking) mainly for use in the production of gasoline.

The steam cracking technique is typically conducted in a manner such that naphtha or kerosene is allowed to react at a high temperature of 800~900° C. for a short residence time in the presence of steam. According to the steam cracking technique, the resultant olefins are of various types and have compositions that are determined within the limited range. In the steam cracking technique, various attempts have been made to correspond to cracking reaction conditions, such as high temperatures and short residence times, and to optimize energy efficiency. However, it is not easy to control the composition of olefins using the present steam cracking technique, and as well, the reaction takes place at 800~900° C. and thus a lot of heat energy is required. Hence, there is a need for continuous advancement of the steam cracking technique.

In addition, light olefin compounds may be produced through FCC. Such an FCC process is a catalytic cracking technique using a catalyst in the form of fine particles which behave like fluid when being aerated using steam. Such a catalytic cracking technique is widely known in the art. Especially, in order to increase the yield of olefin (e.g., propylene) instead of gasoline, DCC (Deep Catalytic Cracking) is known as a modification of the FCC process. In the FCC process, a vacuum residue, an atmospheric residue, or gas oil has been used as the feedstock. However, FCC suffers because olefins are produced as the by-product.

The representative product yields of the above-mentioned processes are shown in Table 1 below.

TABLE 1

|  | Yield through Steam Cracking | Yield through FCC |
|---|---|---|
| Methane | 16.13 | 1.2 |
| Ethylene | 32.05 | 1.9 |
| Ethane | 2.91 | 0.7 |
| Propylene | 16.65 | 4.8 |
| Propane | 0.35 | 0.7 |
| C4 | 10.94 | 9.1 |
| C5 | 5.71 | 1.1 |
| C6 or more | 14.18 | 79.6 |
| Others | 1.08 | 0.9 |

In regard to the production of light olefins, there has been proposed an olefin production process through catalytic cracking, in addition to steam cracking and FCC. Particularly useful is a fluidized bed catalytic cracking process in the presence of a solid acid catalyst containing a large amount of HZSM-5 zeolite. Such olefin production processes through catalytic cracking have been developed to realize high production yields of light olefins using various hydrocarbons as the feedstock. In particular, these processes are characterized by high propylene yields, operation at lower temperatures than steam cracking, and easy recirculation of by-products.

More specifically, the related techniques are as follows.

U.S. Pat. No. 4,065,379 discloses a method of producing light olefins at high yields through FCC using a petroleum distillate, such as a vacuum residue, an atmospheric residue, or gas oil, as a feedstock, which requires a very high reaction temperature and results in an ethylene yield higher than a propylene yield.

U.S. Pat. No. 5,043,522 discloses a method of producing light olefins using a feedstock including 40~95 wt % paraffins and 5~60 wt % olefins through a fluidized bed catalytic cracking process, leading to 50 wt % or less reaction conversion rates.

U.S. Pat. No. 5,770,043 discloses a method of increasing the yield of light olefins using two risers, using a petroleum distillate such as gas oil as a feedstock, and re-circulating naphtha produced as an intermediate.

U.S. Pat. No. 6,307,117 discloses a method of separating a catalytic cracked product into H2~C3 distillates and C4+ distillates. Further, a method of separation of the C4+ distillates into C4, C5~C8 distillates, and C9+ distillates is disclosed. Still further, a method of additionally converting the C4+ distillates using a steam cracking reactor is introduced. However, these methods do not provide operation conditions for efficient use of the reaction product, in consideration of the properties of the catalytic cracking reaction.

U.S. Pat. No. 6,342,153 discloses a method of preparing a catalyst for use in the realization of high light olefin yields through an FCC process in a dilute pneumatic conveying regime using a petroleum distillate such as a vacuum residue, an atmospheric residue or gas oil as a feedstock.

U.S. Pat. No. 6,395,949 discloses a fluidized bed catalytic cracking process for enhancing the production of light olefins and aromatic compounds using a hydrocarbon feedstock and additionally introducing iso-pentane.

U.S. Pat. No. 6,602,920 discloses a process scheme for sequentially using a thermal cracking process, a hydrogenation process, and a catalytic cracking process to produce light olefins using natural gas as a feedstock. However, the process disclosed in this patent cannot be applied to the catalytic cracking process of the present invention using a hydrocarbon feedstock, preferably naphtha or kerosene.

U.S. Pat. No. 6,791,002 schematically discloses a method of connecting a plurality of risers in series or in parallel to increase the production of light olefins and a method for multiple feed streams, but specific reaction conditions and reaction results are not mentioned therein.

U.S. Pat. No. 6,867,341 discloses a catalyst for use in cracking of naphtha by controlling the distribution and crystal size of aluminum present in zeolite and a process therefor. According to this patent, aluminum present outside the pores is chemically neutralized to minimize the production of aromatic compounds on the surfaces of pores, whereas an acid site density is increased inside the pores using a catalyst having a high aluminum ion concentration, thus selectively increasing the production of ethylene and propylene having small sizes. However, only the general operation conditions including temperature and pressure of the catalytic cracking process are mentioned.

In this way, catalytic cracking processes for the production of light olefin hydrocarbons using various hydrocarbons as the feedstock have been actively developed. However, the additional development of processes for selectively producing light olefins, such as ethylene and propylene, from hydrocarbons that have high economic availability and may be used in great quantities as the feedstock, in particular, naphtha or kerosene, at high conversion rates and high selectivity is still urgently required.

In the process for producing light olefin hydrocarbons from hydrocarbon feedstock, preferably naphtha or kerosene, through catalytic cracking, in order to selectively produce light olefins such as ethylene and propylene at high conversion rates and high selectivity, the operation conditions of a riser, in which the catalytic cracking process is mainly conducted, are regarded as important. Especially, the fluidization and reaction in the riser may be more easily understood in consideration of the following theory.

As shown in FIG. 1, when a gas is supplied into the lower portion of a container packed with a solid catalyst, particles are fluidized. At a minimum fluidization velocity or higher, the flow regime is specifically divided into five regimes, including a bubbling regime, a slugging regime, a turbulent regime, a fast fluidization regime, and a dilute pneumatic conveying regime, respectively having different particle mobilities. Thus, in the case of a process using a fluidized bed reactor, a flow regime suitable for each process property should be set.

FIG. 2 shows the volume fraction of the catalyst in the reactor varying depending on the riser height, that is, on the flow regime. As shown in this drawing, it is confirmed that the total amount of the catalyst substantially present in the reactor considerably depends on the change in the flow regime. However, in the reaction involving the use of the catalyst, such as the fluidized bed catalytic cracking process, the total amount of the catalyst positively affects the performance of the process. Hence, the setting of the flow regime through the change in process operation conditions has a great influence on the reaction result.

Moreover, with the intention of determining the flow regime of the riser in the fluidization catalytic cracking process, many variables affecting the catalytic cracking reaction must be considered. As such, such variables include reaction temperatures, endothermic requirements, reaction times, catalyst sizes, catalyst circulation velocities, feedstock and catalyst ratios, inactivation of the catalyst due to the production of coke, strength of the catalyst, etc.

In particular, since the catalytic cracking of the hydrocarbon compound is an endothermic reaction, a lot of heat is required. Thus, in the case of the fluidized bed catalytic cracking process, desired reaction heat may be supplied through the circulation of hot catalyst, which is referred to as a circulating fluidization process. Accordingly, the riser of the circulating fluidization process for catalytic cracking of the hydrocarbon compound is operated in the fast fluidization regime or dilute pneumatic conveying regime, thereby maintaining efficient circulation of the catalyst.

As the typically commercialized catalytic cracking process of the hydrocarbon compound, there is FCC (Fluid Catalytic Cracking) for production of gasoline from petroleum distillate. Presently, the flow regime of the commercialized FCC is mainly operated in the dilute pneumatic conveying regime.

Specific techniques concerning the flow regime are as follows.

U.S. Pat. No. 4,548,138 discloses a combustor used in a fast fluidization regime, and the operation principle and mechanical device thereof are also mentioned.

U.S. Pat. No. 5,012,026 discloses a fluidized bed catalytic cracking process for converting paraffin hydrocarbons into light olefin, in which a turbulent regime is adopted as the main operation condition of the riser. In addition, a heat exchanger is used to supply heat required for an endothermic reaction, and the circulation and regeneration of the catalyst are minimized. However, there is no specific content related to a technique for realizing a high catalyst circulation rate necessary for the catalytic cracking process in the turbulent regime.

Therefore, in the process of producing light olefin hydrocarbons from the hydrocarbon feedstock, preferably naphtha or kerosene, using a fluidized bed catalytic cracking process, the operation conditions of the riser for the reaction, in particular, more efficient flow regime and process conditions thereof, are required.

DISCLOSURE

[Technical Problem]

Accordingly, an object of the present invention is to provide a process of producing light olefin hydrocarbons from a hydrocarbon feedstock, preferably naphtha or kerosene, using a fluidized bed catalytic cracking process, in which a gas flow velocity and a catalyst supply velocity, as operation conditions of a riser for the catalytic cracking, are controlled, thereby providing a flow regime effective for the selective production of light olefins such as ethylene and propylene at high conversion rates and high selectivity.

[Technical Solution]

In order to accomplish the above object, the present invention provides a catalytic cracking process of producing light olefins, comprising (a) supplying a naphtha or kerosene feedstock and dilution steam or lift gas into a riser in which a flow regime is a fast fluidization regime, thus inducing a catalytic cracking reaction in the presence of a catalyst; (b) separating an effluent of the catalytic cracking reaction into the catalyst and a reaction product including ethylene and propylene; (c) stripping the catalyst separated in (b) to remove a hydrocarbon compound contained therein; (d) mixing the catalyst stripped in (c) with an oxygen-containing gas, such as air, thus continuously regenerating the catalyst; (e) circulating the catalyst regenerated in (d) into (a), thus re-supplying it into the riser; and (f) cooling, compressing and separating the hydrocarbon compound as the reaction product separated in (b), thus preparing a light olefin product.

[Advantageous Effects]

According to the present invention, in the process of producing light olefin hydrocarbons from a hydrocarbon feedstock, for example, naphtha or kerosene, using a fluidized bed catalytic cracking process, the gas flow velocity and catalyst supply velocity, as the operation conditions of the riser for use in the catalytic cracking, are controlled, such that the flow regime of the riser is maintained as a fast fluidization regime. Thereby, it is possible to provide a flow regime effective for the selective production of light olefins such as ethylene and propylene at high conversion rates and high selectivity through maximization of the volume fraction of the catalyst in the riser.

Figure 1:
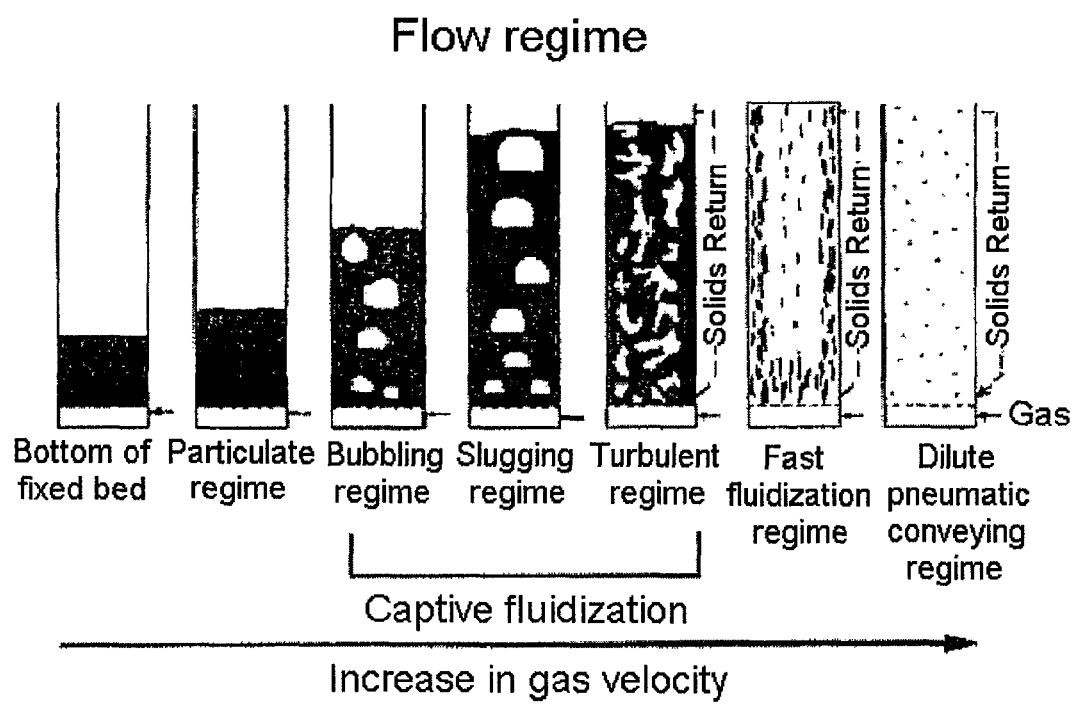
FIG. 1 is a view showing the general change in the fluidized bed in the flow regime depending on variation in gas velocity.
Figure 2:
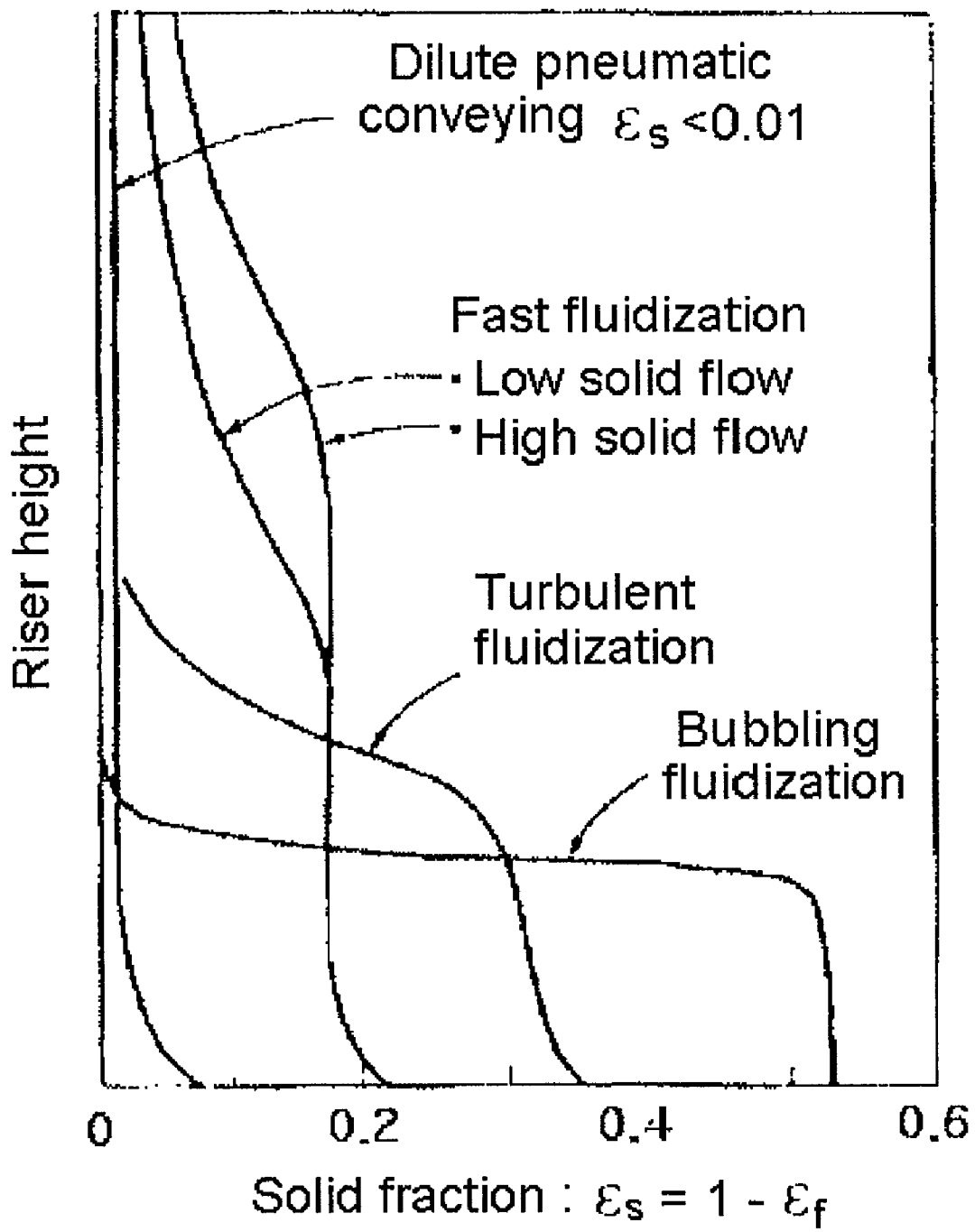
FIG. 2 is a view showing the volume fraction of a catalyst in the fluidized bed varying along the riser height.

<Description of the Reference Numerals in the Drawings>

| 1: | riser |
|---|---|
| 2: | stripper |
| 3: | regenerator |
| 11: | supply line of hydrocarbon feedstock |
| 12: | supply line of dilution steam or lift gas |
| 13: | regenerator stand pipe |
| 15: | gas reaction product |
| 16: | supply line of stripping steam |
| 17: | stripper stand pipe |
| 18: | stripper slide valve |
| 19: | flue gas |
| 20: | oxygen-containing gas, such as air |
| 21: | regenerator slide valve |
| 51: | riser of cold model |
| 52: | cyclone of cold model |
| 53: | stand pipe of cold model |
| 54: | loop seal of cold model |
| 60: | main gas supply line of cold model |
| 61: | gas supply line for control of catalyst circulation of cold model |
| 62: | gas supply line of stand pipe of cold model |
| 63: | flue gas of cold model |

BEST MODE

Hereinafter, a detailed description will be given of the present invention.

In the present invention, the catalytic cracking process of producing light olefins comprises (a) supplying a hydrocarbon feedstock and dilution steam or lift gas into a riser in which a flow regime is a fast fluidization regime, thus inducing a catalytic cracking reaction in the presence of a catalyst; (b) separating effluent of the catalytic cracking reaction into the catalyst and a reaction product including ethylene and propylene; (c) stripping the catalyst separated in (b) to remove hydrocarbon compounds contained therein; (d) mixing the catalyst stripped in (c) with an oxygen-containing gas, such as air, thus continuously regenerating the catalyst; (e) circulating the catalyst regenerated in (d) into (a), thus re-supplying it into the riser; and (f) cooling, compressing and separating the hydrocarbon compound as the reaction product separated in (b), thus preparing a light olefin product.

The catalytic cracking process according to the embodiment of the present invention is specifically described below, with reference to FIG. 3, but the scope of the present invention is not limited thereto.

The feedstock mentioned above is supplied through line 11 of FIG. 3. In this case, for more efficient reaction, the feedstock may be heated at 30~600° C. and then supplied. In addition, the feedstock may be supplied in the form of gas or dispersed liquid depending on the composition thereof, however the present invention is not limited thereto. The feedstock of the line 11 is mixed with dilution steam or lift gas supplied through a line 12 and is thus introduced into a riser 1 that is a reaction zone, and is further mixed with a regenerated catalyst, which is supplied through the regenerator stand pipe of a line 13, in the lower portion of the riser 1. The steam or lift gas 12 is effectively supplied at a weight ratio of 0.01~10, and preferably 0.1~2.0 relative to the feedstock, and functions to increase the selectivity of light olefin hydrocarbon while making the flow of the regenerated catalyst efficient. In addition, the process of mixing the feedstock, the steam or lift gas, and the regenerated catalyst may be realized through various methods known in the art, which are incorporated in the scope of the present invention.

The catalyst used in the process, that is, the regenerated catalyst, is supplied into the riser 1 via the line 13 from a regenerator 3. As such, the temperature is preferably maintained at 550~800° C. That is, heat supplied by the regenerated catalyst 13 enables thorough gasification of the feedstock 1 and the steam or lift gas 12 and realization of the temperature required for the catalytic cracking reaction.

Subsequently, the feedstock and the catalyst mixed in the lower portion of the riser 1 are fluidized and moved toward the upper portion thereof while being subjected to catalytic cracking in the riser 1. In such a case, when the catalytic cracking reaction, which is an endothermic reaction, takes place, the temperature of the mixture decreases and thus the temperature of the upper portion of the riser 1 is relatively lowered. The reaction product and the catalyst reaching the upper portion of the riser 1 are fed into a stripper 2, such that the gas reaction product and the solid catalyst are separated from each other within a short time. In order to increase the efficiency of such separation, a cyclone may be selectively used. The separated gas product is discharged through a line 15, and the separated catalyst is moved downward in the stripper 2 and accumulates therein. As such, stripping steam is supplied into the lower portion of the stripper 2 through a line 16. While the stripping steam 16 flows upward along the stripper 2, it functions to remove a non-separated hydrocarbon reaction product contained in the catalyst, which is then discharged through a gas reaction product line 15.

The catalyst situated in the lower portion of the stripper 2 is transferred into the regenerator 3 via the stripper stand pipe of a line 17 under the control of a slide valve 18. At this time, the catalyst may contain coke produced during the reaction. Into the regenerator 3, an oxygen-containing gas such as air is supplied through a line 20, such that the coke contained in the catalyst reacts with oxygen at a high temperature of 600° C. or more to convert it into carbon monoxide or carbon dioxide, which is then discharged as flue gas through a line 19. Thereby, the amount of coke included in the catalyst may be drastically decreased.

The regenerated catalyst present in the lower portion of the regenerator 3 is supplied again into the riser via the regenerator stand pipe of the line 13 under the control of the slide valve 21, and thus may be recirculated in the process.

According to the process of the present invention, as the feedstock, a hydrocarbon compound, specifically, full-range naphtha or kerosene, more specifically, a hydrocarbon mixture having a boiling point of 30~350° C. may be used. Preferably, such a hydrocarbon mixture is exemplified by naphtha containing $C_{2-15}$ hydrocarbon, and more preferably by full-range naphtha containing 60~90 wt % paraffin (n-paraffin and i-paraffin) and not more than 20 wt % olefin. In addition, the feedstock used in the process of the present invention includes a mixture of naphtha and $C_{4-5}$ hydrocarbon remaining after separation/recovery of light olefin.

Further, the catalyst used for catalytic cracking of the feedstock is not particularly limited so long as it is generally known in the art as being able to convert a hydrocarbon compound into light olefin through a catalytic cracking reaction. Preferably, a zeolite compound, and more preferably, a HZSM-5 type zeolite-containing solid acid catalyst, is used. Moreover, in order to increase the production of light olefin, the use of a predetermined amount of HZSM-5 is effective. The solid acid catalyst is composed of silica or alumina, and may also include metal. Furthermore, the solid acid catalyst has an average size of 20~2000 μm, preferably 40~200 μm, and more preferably 60~150 μm.

As mentioned above, the catalytic cracking reaction for conversion of the hydrocarbon feedstock into light olefins takes place in the riser 1. Thus, main reaction conditions affecting the yield of light olefin include the temperature in the riser, the dilution proportion of the feedstock by the dilution steam or lift gas, the residence time of the reaction material in the riser, the volume fraction and distribution of the catalyst in the riser, etc., which are specifically described below.

The temperature of the riser is the highest at the lower portion thereof, and then decreases toward the upper portion thereof. Thus, it is effective for the temperature of the lower portion of the riser to be maintained at 550~800° C., preferably 630~760° C., and more preferably 650~740° C., whereas the temperature of the upper portion of the riser should be maintained at 500~720° C., preferably 600~700° C., and more preferably 640~690° C., provided that the temperature of the lower portion of the riser is higher than that of the upper portion thereof for efficient flow.

The dilution steam or lift gas is not particularly limited so long as it is known in the art, and functions to make the flow of the regenerated catalyst efficient and also to decrease the partial pressure of hydrocarbon in the riser so as to increase the selectivity of light olefins. Therefore, the dilution steam or lift gas may serve as an important reaction condition affecting the yield of light olefin. Accordingly, the dilution steam or lift gas is supplied at a weight ratio of 0.01~10, and preferably 0.1~2.0 relative to the feedstock.

In the catalytic cracking process for the production of light olefin using the zeolite-based solid acid catalyst, the residence time of the reaction material in the riser may also act as an important reaction condition determining the yield and composition of light olefin. While conducting the catalytic cracking reaction through the riser, since the molecular number and flow velocity of the gas change, a criterion for determining the residence time is required. In the present invention, the residence time of the reaction material in the riser is determined to be a numerical value obtained by dividing the volume of the riser by the volume velocity of the gas discharged from the upper portion of the riser. In the catalytic cracking process of the present invention, the residence time of the hydrocarbon feedstock in the riser is 0.01~600 sec, preferably 0.1~60 sec, and more preferably 0.5~5 sec.

The fluidized bed catalytic cracking reaction of the present invention is an endothermic reaction, and thus heat required for the reaction is supplied through the recirculation of the hot catalyst. In the present invention, the amount of recirculated catalyst is in the range of 10~100, and preferably 20~60 at a weight ratio that is obtained by dividing the weight of the recirculated catalyst by the weight of feedstock (naphtha or kerosene).

The volume fraction and distribution of the catalyst in the riser are greatly affected by the flow regime. As such, the flow regime is determined by the gas velocity in the riser and the velocity of the catalyst to be supplied into the riser.

In the catalytic cracking process of the present invention, it is important to provide the volume fraction and distribution of the catalyst so as to induce the catalytic cracking reaction in the fast fluidization regime, as the flow regime of the riser, for the effective production of the light olefin hydrocarbon from the hydrocarbon feedstock using the catalytic cracking process of producing light olefins.

Accordingly, the range of the fast fluidization regime should be more definitely determined. To this end, this fast fluidization regime is mentioned compared to the turbulent regime and the dilute pneumatic conveying regime adjacent thereto. As the gas flow velocity increases, transition from the turbulent regime to the fast fluidization regime in which solid particles are drastically entrained and thus removed from the riser takes place. Thus, in order to maintain the amount of the catalyst in the riser at the gas velocity of the fast fluidization regime, the catalyst must be continuously supplied into the lower portion of the riser. In the fast fluidization regime, the volume fraction of the catalyst varies along the riser height, and a dense region and a dilute region are present in the lower portion and the upper portion of the riser, respectively.

Moreover, in the fast fluidization regime, when the velocity of the gas flowing upward is further increased or the influx of solid particles is decreased, the volume of the catalyst in the riser decreases and thus transition to the dilute pneumatic conveying regime takes place. In the dilute pneumatic conveying regime, the volume fraction of the catalyst is very low, and also is only slightly affected by the riser height.

As such, the volume of the catalyst means a volumetric space occupied by the catalyst, with the exception of interstitial space of the catalyst particles, in a predetermined unit volume. In the case of a porous catalyst, its volume contains macropores and micropores in the catalyst.

In addition, Kunii and Levenspiel (1991, Fluidization Engineering) have disclosed the continuous supply of the catalyst to maintain the operation conditions in a normal state because the entrainment of the catalyst allowing the catalyst to be removed from the riser takes place rapidly in the fast fluidization regime. As shown in FIG. 3, the fast fluidization regime is characterized as follows.

The volume fraction of the catalyst is 0.2~0.4 relative to the volume of the riser in a short length section from the inlet of the lower portion of the riser.

The volume fraction of the catalyst is constant at about 0.2 in a section between the lower portion of the riser and a predetermined height from the lower portion. Such a section therebetween is called the dense region.

The volume fraction of the catalyst gradually varies in a section above the dense region and thus is in the range of 0.02~0.05.

Although the qualitative properties of the fast fluidization regime are invariable under various process conditions, the quantitative numerical value of the volume of the catalyst varies. The quantitative value of the volume of the catalyst is changed depending on the physical properties of the catalyst, that is, the inherent density and sphericity of the catalyst, and also depending on the physical properties of gas, such as the density and viscosity of the gas due to the change in the type of gas.

Therefore, the preferred fast fluidization regime for the fluidization catalytic cracking process of the hydrocarbon compound according to the present invention is formed in such a manner that the gas flow velocity in the riser is maintained higher than in the turbulent regime and lower than in the dilute pneumatic conveying regime, and that a normal state for continuously supplying the predetermined amount of the catalyst into the riser is maintained. Moreover, the fast fluidization regime is represented by a flow regime in which the volume fraction of the catalyst varies along the riser height and which has the dense region present in the lower portion of the riser and the dilute region present in the upper portion of the riser. More particularly, the fast fluidization regime may be formed and defined as follows.

1) The gas velocity should be maintained not lower than a gas flow velocity required to efficiently remove the catalyst from the upper portion of the riser through entrainment, and the catalyst should be continuously supplied into the lower portion of the catalyst.

2) As the gas flow velocity increases under the above conditions, the difference between the volume fractions of the catalyst at the ¼ point and the ¾ point from the lower portion of the riser decreases. The velocities of gas and catalyst are controlled, and therefore the difference between the volume fractions of the catalyst of the above two points is maintained at 0.02 or more, and preferably 0.04 or more.

In the process of producing the light olefin hydrocarbon from the hydrocarbon feedstock, preferably full-range naphtha or kerosene using a fluidized bed catalytic cracking process, the gas velocity in the riser and the velocity of the catalyst to be supplied into the riser are controlled under the above conditions to induce the reaction in the fast fluidization regime, thus realizing the maximum concentration of the catalyst in the riser. Thereby, the light olefin hydrocarbons, preferably ethylene and propylene, may be provided at high conversion rates and high selectivity.

[Mode For Invention]

A better understanding of the present invention may be obtained through the following examples which are set forth to illustrate, but are not to be construed to limit the present invention.

COMPARATIVE EXAMPLE 1

Dilute Fluidization Regime

A. Fabrication of Cold Model

Figure 4:
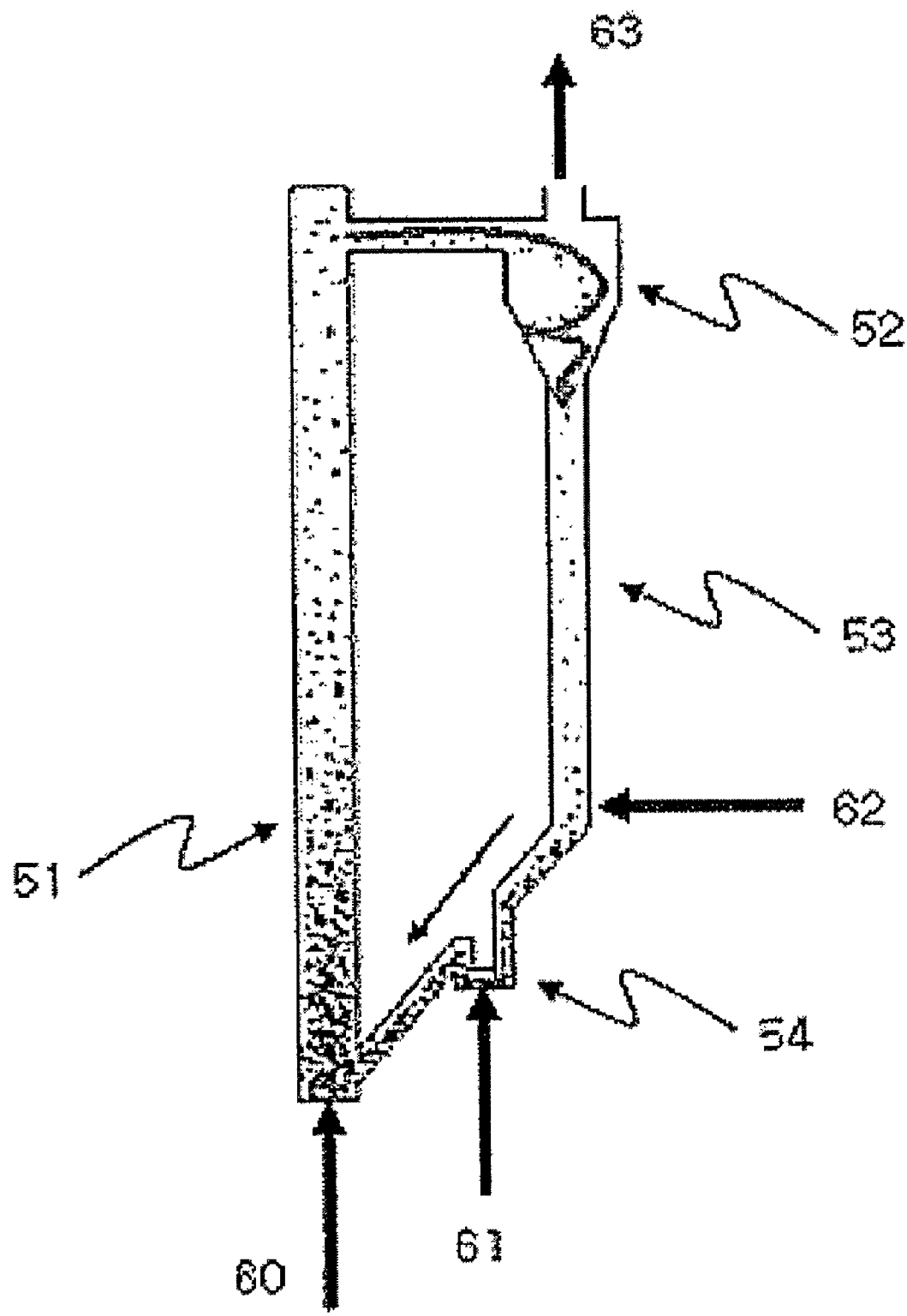
FIG. 4 is a schematic view showing a fluidized bed cold model for use in testing the flow regime at room temperature.

In order to confirm variation in the flow regime depending on the velocities of gas and catalyst at room temperature, a fluidized bed cold model was fabricated as shown in FIG. 4. Solid particles passed through a loop seal 54 for controlling a solid circulating velocity were supplied into a riser 51 of the cold model and then transferred upward along the riser by main gas supply through a line 60. Subsequently, the gas was separated from the solid using a cyclone of the cold model, after which the gas was discharged as flue gas through a line 63, and the solid was transferred downward along a stand pipe of the cold model. As such, the solid was efficiently circulated by gas supplied through a line 62. The loop seal 54 of the cold model was used to control the amount of catalyst to be circulated, by the use of gas supplied through a line 61 of the cold model for controlling catalyst circulation.

In Comparative Example 1, the riser of the cold model was fabricated to have a height of 2.5 m and a diameter of 0.9 cm, and the stand pipe and the loop seal were fabricated for easy circulation of the catalyst.

B. Catalyst

The catalyst used in the test had an average diameter of 84 µm and particle size distribution of 10% of 57 µm or less, 40% of 57~84 µm, 40% of 84~115 µm, and 10% of 115 µm or more.

C. Test for Flow Regime

Figure 5:
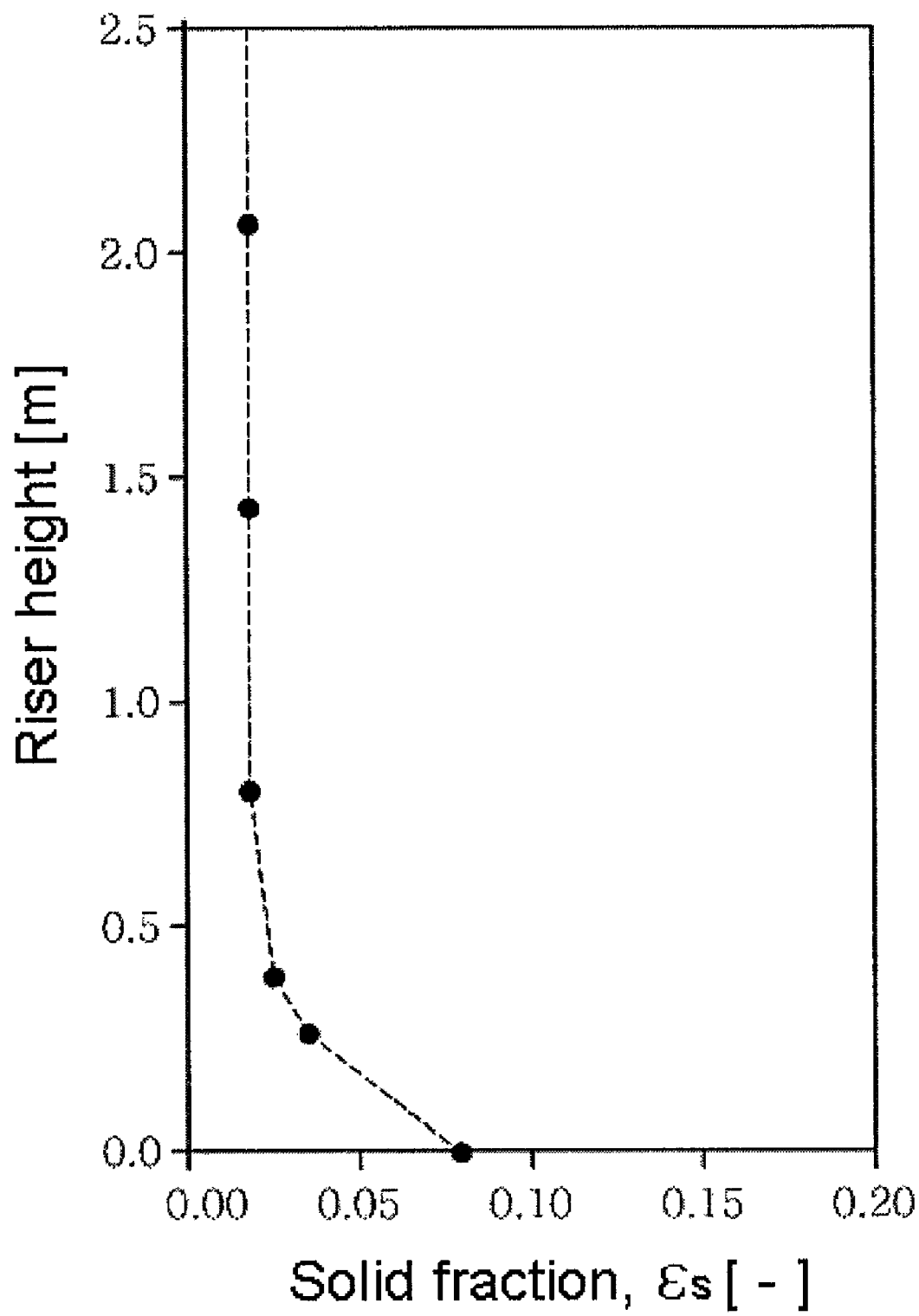
FIG. 5 is a graph showing the volume fraction of the catalyst in the fluidized bed in the dilute pneumatic conveying regime, as the result of test of the cold model of Comparative Example 1.

The test was conducted at room temperature under atmospheric pressure, and air was used as a fluidization gas. The velocity of the fluidization gas was 2.2 m/s, and the velocity of the catalyst to be circulated into the inlet of the lower portion of the riser was 20.2 kg/hr, corresponding to 88.1 kg/m²s in the riser. Under the above conditions, the pressure drop value was measured along the riser height, and thus the volume fraction of the catalyst, that is, the solid fraction, was obtained (FIG. 5). In FIG. 5, the solid fractions were 0.049 and 0.040 at the ¼ point and ¾ point from the lower portion of the riser, respectively, and the difference therebetween was 0.009. According to the definition of the present invention, the flow regime was confirmed to be a dilute pneumatic conveying regime.

EXAMPLE 1

Fast Fluidization Regime

A. Fabrication of Cold Model

A cold model was fabricated in the same manner as in Comparative Example 1, as shown in FIG. 4.

B. Catalyst

The same catalyst as that used in Comparative Example 1 was used.

C. Test for Flow Regime

Figure 6:
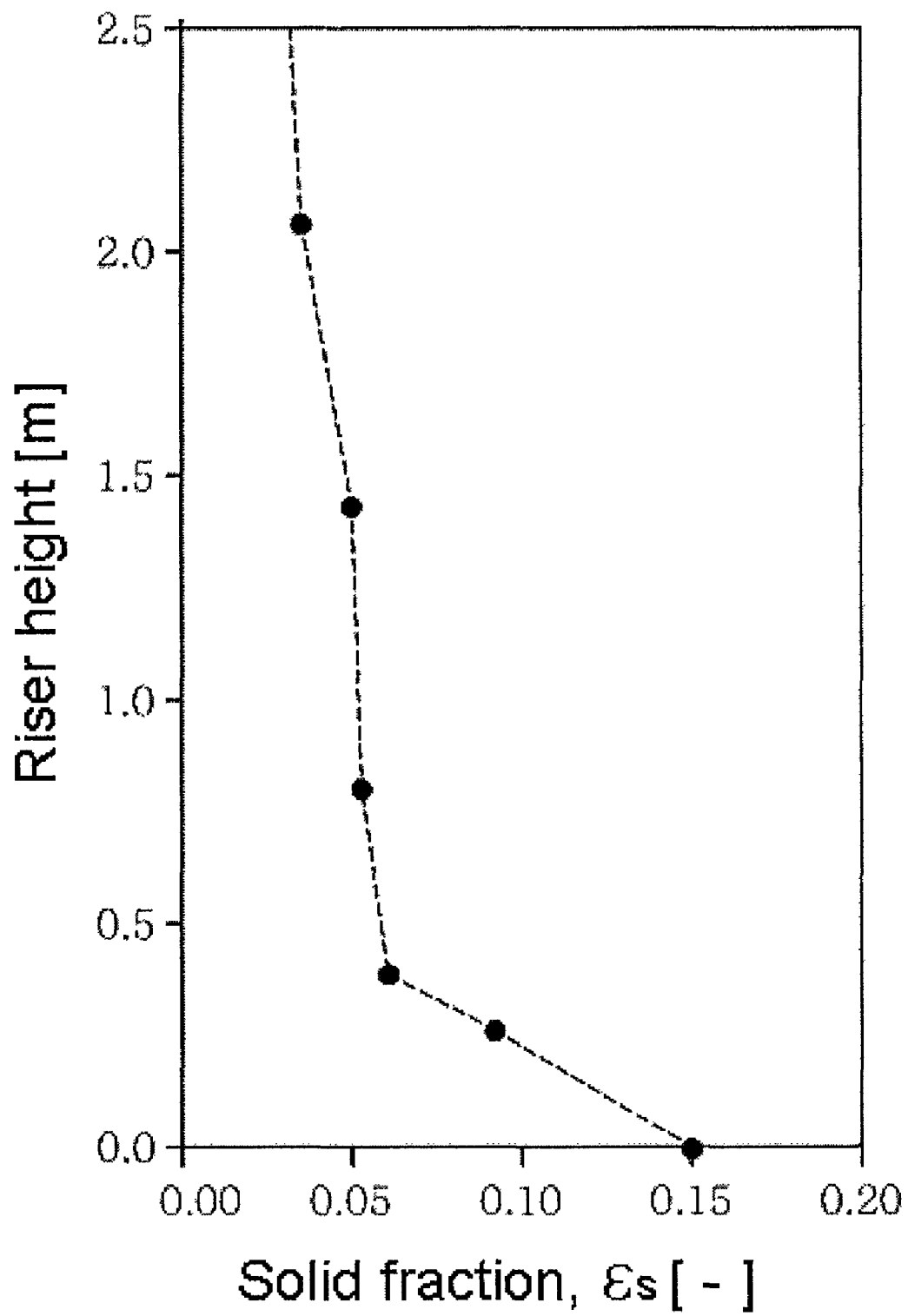
FIG. 6 is a graph showing the volume fraction of the catalyst in the fluidized bed in the fast fluidization regime, as the result of test of the cold model of Example 1.

The test was conducted in the same manner as in Comparative Example 1. The velocity of the fluidization gas was 0.83 m/s, and the velocity of the catalyst to be circulated into the inlet of the lower portion of the riser was 7.7 kg/hr, corresponding to 33.6 kg/m²s in the riser. Under the above conditions, the pressure drop value was measured along the riser height, and thus the solid fraction was obtained (FIG. 6). In FIG. 6, the solid fractions were 0.092 and 0.049 at the ¼ point and ¾ point from the lower portion of the riser, respectively, the difference therebetween being 0.043. According to the definition of the present invention, the flow regime could be confirmed to be a fast fluidization regime.

COMPARATIVE EXAMPLE 2

A. Preparation of Catalyst

HZSM-5 (Si/Al=25, Zeolyst) and conc. phosphoric acid (85% $H_3PO_4$) were added to distilled water and stirred for about 20 min. This mixture was added with $La(NO_3)_3 \cdot xH_2O$ and its pH was maintained at 7~8 using ammonia water and stirred at about 45° C. for about 20 min. Subsequently, the reaction mixture was stirred at about 50° C. until all of the water had evaporated, and then vacuum filtered, thus separating a solid product. The separated solid product was burned at about 500° C. for 5 hours in air, thus preparing a La—$H_3PO_4$—HZSM-5 catalyst. The weight ratios of material used were 10.00 of HZSM-5 (Si/Al=25, Zeolyst), 0.74 of conc. Phosphoric acid (85% $H_3PO_4$), and 1.40 of $La(NO_3)_3$ $xH_2O$, based on 100 of distilled water.

Further, slurry comprising 6.6 kg of the La—$H_3PO_4$—HZSM-5 catalyst thus prepared, 0.7 kg of Y zeolite, and 3 kg of an alumina binder was stirred and spray dried, thus preparing a catalyst having an average size of 80 μm.

B. Treatment of Catalyst with Steam

In order to evaluate performance of the catalyst at equilibrium, the catalyst was maintained at 760° C. for 24 hours in a 100% steam atmosphere.

C. Production of Light Olefin

Figure 3:
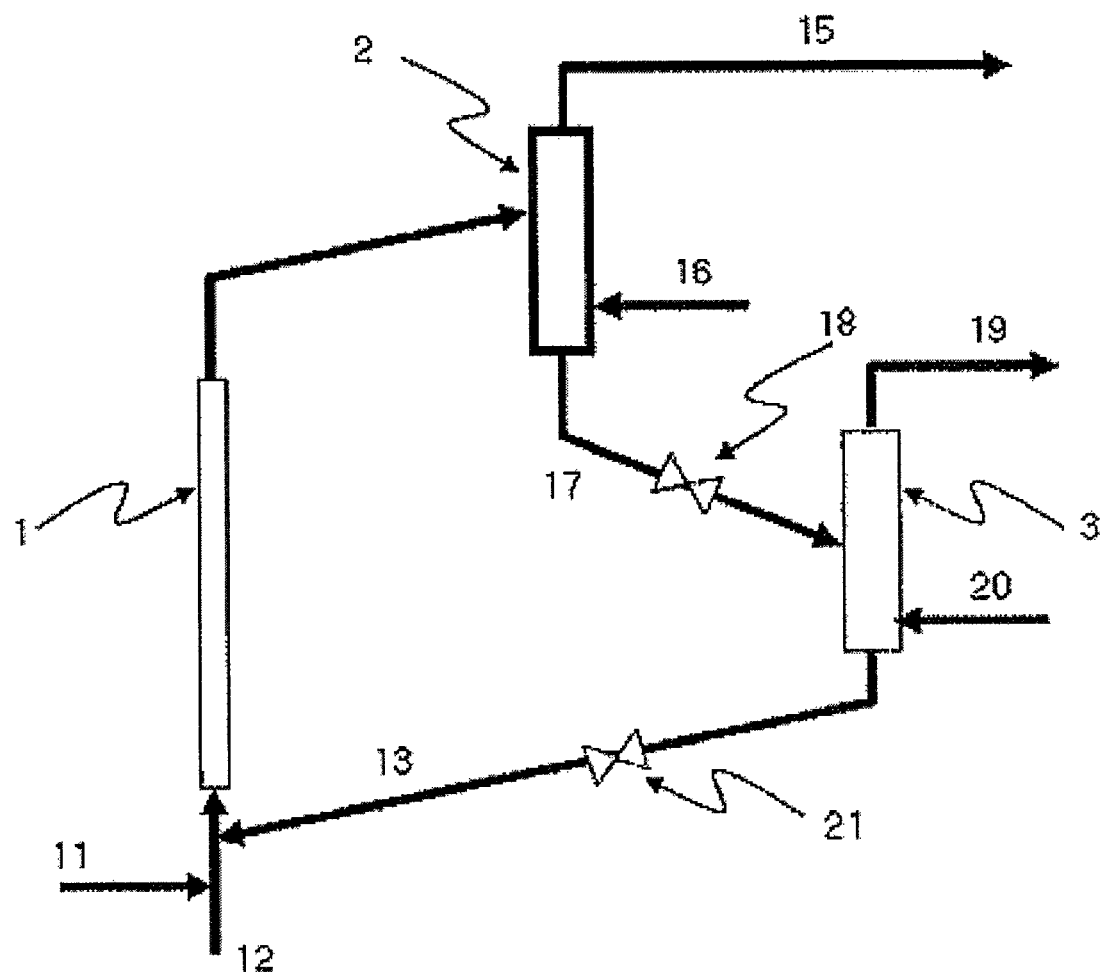
FIG. 3 is a view schematically showing the catalytic cracking process of producing light olefins used in the present invention.

In Comparative Example 2, to measure the activity of the catalyst during the process of producing light olefin as in FIG. 3, a fluidized bed reaction system was used. The fluidized bed reaction system was composed of a riser, a regenerator, a stripper, and a stabilizer. The riser had a height of 6.5 m and a diameter of 0.94 cm, the regenerator had a height of 1.5 m and a diameter of 12 cm, the stripper had a height of 2 m and a diameter of 10 cm, and the stabilizer had a height of 1.7 m and a diameter of 15 cm.

As the feedstock, typical naphtha resulting from a refining process was used, the specific composition thereof being shown in Table 2 below.

TABLE 2

|  | n-Paraffin | i-Paraffin | Naphthene | Aromatic |
|---|---|---|---|---|
| Naphtha | 36.2% | 49.3% | 11.3% | 3.2% |

The feedstock, the steam and the catalyst were supplied into the inlet of the riser and thus mixed together, the feedstock having conditions of 390 g/hr and 400° C., the steam having conditions of 195 g/hr and 400° C., and the catalyst having conditions of 22000 g/hr and 725° C. In consideration of the sectional area of the riser, the catalyst was supplied in an amount of 88.1 kg/m$^2$s (the same as that of the cold model of Comparative Example 1). Further, with the goal of efficiently circulating the solid catalyst in the interest of the properties of the test system, 60 L/hr of nitrogen was used for introduction of the regenerated catalyst.

In Comparative Example 2, the total velocity of the gas gasified at the inlet of the riser was 2.2 m/s, the same as in Comparative Example 1. In consideration of the density and viscosity of the gas, it was believed that the risers of Comparative Examples 1 and 2 were operated in the same flow regime, that is, the dilute pneumatic conveying regime.

In Comparative Example 2, based on the gas velocity at an outlet of the riser, the residence time of the gas in the riser was 2.2 sec, and the ratio of the weight of feedstock per time to the weight of steam and nitrogen per time, as the dilution proportion supplied into the inlet of the riser, was 0.6. In addition, the ratio of the weight of the feedstock supplied into the inlet of the riser per time to the weight of the regenerated catalyst supplied thereto per time was 56.

The fluidized bed catalytic cracking reaction occurred through the riser, and the conditions of the outlet of the riser were 675° C. and 25 psig. Subsequently, the mixture passed through the riser was separated into the catalyst and distillate at 500° C. using a stripper. Then, the catalyst was circulated into the regenerator, while the distillate was supplied into the stabilizer. The catalyst introduced into the regenerator was brought into contact with air and thus regenerated at 725° C., after which the regenerated catalyst was supplied again into the riser. However, the distillate introduced into the stabilizer was separated into gas and liquid at −10° C.

After the reaction, the gas product was quantitatively analyzed through on-line gas chromatography (Model Name: HP 6890N). Meanwhile, the liquid product was recovered into a storage tank and then quantitatively analyzed using gas chromatography (Model Name: DS 6200).

The results of the conversion rate and weight ratio of the reaction product are shown in Table 3 below.

TABLE 3

|  | Reaction Product (wt %) |
|---|---|
| Methane | 11.0 |
| Ethylene | 14.6 |
| Ethane | 6.0 |
| Propylene | 16.9 |
| Propane | 1.7 |
| C4 | 9.2 |
| C5 | 8.3 |
| C6 or more | 27.4 |
| Others | 4.9 |

EXAMPLE 2

A. Preparation of Catalyst

A catalyst was prepared in the same manner as in Comparative Example 2.

B. Treatment of Catalyst with Steam

The catalyst was treated with steam in the same manner as in Comparative Example 2.

C. Production of Light Olefin

In Example 2, a fluidized bed reaction system the same as in Comparative Example 2 was used, with the exception of the riser. As such, the riser had a height of 2.4 m and a diameter of 0.94 cm.

A feedstock having a composition the same as in Comparative Example 2 was used, and the feedstock had conditions of 150 g/hr and 400° C., the steam had conditions of 45 g/hr and 400° C., and the catalyst had conditions of 8400 g/hr and 725° C. In consideration of the sectional area of the riser, the catalyst was supplied in an amount of 33.6 kg/m$^2$s (the same as that of the cold model of Example 1). Further, in order to efficiently circulate the solid catalyst in the interest of properties of the test system, 60 L/hr of nitrogen was used for introduction of the regenerated catalyst.

In Example 2, the total velocity of the gas gasified at the inlet of the riser was 0.83 m/s, which was the same as in Example 1. Considering the gas density and viscosity, it was believed that the risers of Examples 1 and 2 were operated in the same flow regime, that is, the fast fluidization regime.

In Example 2, the residence time of the gas, the dilution proportion at the inlet of the riser, and the ratio between the weights of the feedstock and the regenerated catalyst supplied into the inlet of the riser per time were the same as in Example 1.

The results of the conversion rate and weight ratio of the reaction product are shown in Table 4 below.

TABLE 4

|  | Reaction Product (wt %) |
|---|---|
| Methane | 13.5 |
| Ethylene | 20.9 |
| Ethane | 8.3 |
| Propylene | 20.1 |
| Propane | 1.9 |
| C4 | 6.9 |
| C5 | 3.6 |
| C6 or more | 19.9 |
| Others | 4.9 |

In terms of the reaction product yields, the yields of light olefins, in particular, ethylene and propylene, of Example 2 were much higher than those of Comparative Example 2.

Thereby, the catalytic cracking reaction in the fast fluidization regime of the present invention could be confirmed to provide more efficient process conditions.

That is, the velocity of the gas and the amount of the catalyst controlled in the cold models of Comparative Example 1 and Example 1 were set the same as in the flow regime of the catalyst under the reaction conditions of Comparative Example 2 and Example 2. Through a general method of confirming the flow of the fluidized bed reactor using the cold model as mentioned above, it can be understood that the riser of Comparative Example 2 was operated in the dilute pneumatic conveying regime the same as in Comparative Example 1, and the riser of Example 2 was operated in the fast fluidization regime the same as in Example 1.

Therefore, as the result of the reaction product yields, light olefins of Example 2, for example, ethylene and propylene, can be generated at very high yields. Compared to the result of Comparative Example 2, the result of Example 2 can be found to be based on the operation in the fast fluidization regime.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A catalytic cracking process of producing light olefins, comprising:
    (a) supplying a paraffinic naphtha or kerosene feedstock and dilution steam or lift gas into a riser in which a flow regime is a fast fluidization regime, thus inducing a catalytic cracking reaction in the presence of a catalyst, the feedstock containing not more than 20 wt % olefins;
    (b) separating an effluent of the catalytic cracking reaction into the catalyst and a reaction product including ethylene and propylene;
    (c) stripping the catalyst separated in step (b) to remove a hydrocarbon compound contained therein;
    (d) mixing the catalyst stripped in step (c) with an oxygen-containing gas at 600° C. or more to remove coke contained therein, thus continuously regenerating the catalyst;
    (e) circulating the catalyst regenerated in step (d) into step (a), thus re-supplying regenerated catalyst into the riser; and
    (f) cooling, compressing and separating the hydrocarbon compound as the reaction product separated in step (b), thus preparing a light olefin product,
    wherein the catalyst is a solid acid catalyst for use in conversion into light olefins, the solid acid catalyst is the zeolite compound HZSM-5, and the catalyst has an average size of 40~200 µm;
    wherein the light olefin product prepared in step (f) contains ethylene of higher than 14.6 wt % and propylene of higher than 16.9 wt %; and
    wherein the catalyst used in step (a) is the regenerated catalysts circulated from step (e).

2. The process according to claim 1, wherein the fast fluidization regime is formed by maintaining a normal state in which the catalyst is continuously supplied in a predetermined amount into the riser while a gas flow velocity in the riser is maintained higher than in a turbulent regime and lower than in a dilute pneumatic conveying regime, and is a flow regime in which a volume fraction of the catalyst varies along a height of the riser, and which has a dense region present in a lower portion of the riser and a dilute region present in an upper portion thereof.

3. The process according to claim 2, wherein, in the fast fluidization regime, i) the catalyst is continuously supplied into the lower portion of the riser while the velocity of the gas is maintained not lower than a gas flow velocity required to efficiently remove the catalyst from the upper portion of the riser through entrainment, and ii) a difference between the volume fractions of the catalyst at a ¼ point and a ¾ point from the lower portion of the riser decreases as the gas flow velocity increases under the conditions of i), such that the difference therebetween is 0.02 or more through control of the gas flow velocity and catalyst supply velocity.

4. The process according to claim 3, wherein the difference between the volume fractions of the catalyst at the ¼ point and the ¾ point from the lower portion of the riser is 0.04 or more.

5. The process according to claim 1, wherein the naphtha or kerosene is a hydrocarbon feedstock having a boiling point of 30~350° C.

6. The process according to claim 1, wherein the naphtha or kerosene comprises 60~90 wt % paraffin (n-paraffin and i-paraffin).

7. The process according to claim 1, wherein a temperature of the lower portion of the riser is 550~800° C., and a temperature of the upper portion of the riser is 550~720° C., the temperature of the lower portion of the riser being maintained higher than that of the upper portion of the riser.

8. The process according to claim 7, wherein the temperature of the lower portion of the riser is 630~760° C., and the temperature of the upper portion of the riser is 600~700° C.

9. The process according to claim 8, wherein the temperature of the lower portion of the riser is 650~740° C., and the temperature of the upper portion of the riser is 640~690° C.

10. The process according to claim 1, wherein a residence time of the naphtha or kerosene in the riser for the catalytic cracking reaction is 0.1~600 sec.

11. The process according to claim 10, wherein the residence time is 0.1~60 sec.

12. The process according to claim 11, wherein the residence time is 0.5~5 sec.

13. The process according to claim 1, wherein a weight ratio obtained by dividing a weight of the catalyst re-supplied into the lower portion of the riser in (e) by a weight of the naphtha or kerosene feedstock is 10~100.

14. The process according to claim 13, wherein the weight ratio is 20~60.

15. The process according to claim 1, wherein the dilution steam or lift gas is supplied into the riser at a weight ratio of 0.01~10 relative to the naphtha or kerosene feedstock.

16. The process according to claim 15, wherein the weight ratio is 0.1~2.0.

17. A catalytic cracking process of producing light olefins, comprising:
    (a) supplying a naphtha or kerosene feedstock containing 60-90 wt % paraffin (n-paraffin and i-paraffin) and dilution steam or lift gas into a riser in which a flow regime is a fast fluidization regime, thus inducing a catalytic cracking reaction in the presence of a catalyst;
    (b) separating an effluent of the catalytic cracking reaction into the catalyst and a reaction product including ethylene and propylene;
    (c) stripping the catalyst separated in step (b) to remove a hydrocarbon compound contained therein;

(d) mixing the catalyst stripped in step (c) with an oxygen-containing gas, thus continuously regenerating the catalyst;

(e) circulating the catalyst regenerated in step (d) into step (a), thus re-supplying it into the riser; and (f) cooling, compressing and separating the hydrocarbon compound as the reaction product separated in step (b), thus preparing a light olefin product, wherein the catalyst is a solid acid catalyst for use in conversion into light olefins, the solid acid catalyst is the zeolite compound HZSM-5, and the catalyst has an average size of 40~200 μm, and wherein the light olefin product prepared in step (f) contains at least 20 wt % more ethylene and at least 20 wt % more propylene than the ethylene and propylene contained in the naphtha or kerosene feedstock.

18. The process according to claim 17, wherein the catalyst in step (d) is mixed with an oxygen-containing gas at 600° C. or more to remove coke contained therein to regenerate the catalyst and wherein the catalyst circulated in step (e) is only the regenerated catalyst.

19. The process according to claim 1, wherein the light olefin product prepared in step (f) contains at least 20 wt % ethylene and at least 20 wt % propylene.

* * * * *